(12) United States Patent
Sudo et al.

(10) Patent No.: US 9,708,730 B1
(45) Date of Patent: Jul. 18, 2017

(54) QUALITY-EVALUATED VITREOUS SILICA CRUCIBLE

(71) Applicant: SUMCO CORPORATION, Minato-ku, Tokyo (JP)

(72) Inventors: Toshiaki Sudo, Akita (JP); Tadahiro Sato, Akita (JP); Ken Kitahara, Akita (JP); Masami Ohara, Akita (JP)

(73) Assignee: SUMCO CORPORATION, Tokyo (JP)

( * ) Notice: Subject to any disclaimer, the term of this patent is extended or adjusted under 35 U.S.C. 154(b) by 0 days.

(21) Appl. No.: 15/488,342

(22) Filed: Apr. 14, 2017

Related U.S. Application Data

(63) Continuation of application No. 15/377,963, filed on Dec. 13, 2016, now Pat. No. 9,653,268, which is a continuation of application No. 14/901,030, filed as application No. PCT/JP2013/067946 on Jun. 30, 2013, now Pat. No. 9,557,276.

(51) Int. Cl.
| | | |
|---|---|---|
| G01N 21/00 | (2006.01) | |
| C30B 15/10 | (2006.01) | |
| C30B 29/06 | (2006.01) | |
| C30B 15/14 | (2006.01) | |
| C30B 15/00 | (2006.01) | |
| C30B 35/00 | (2006.01) | |
| G01N 21/65 | (2006.01) | |

(52) U.S. Cl.
CPC .............. *C30B 15/10* (2013.01); *C30B 15/14* (2013.01); *C30B 29/06* (2013.01); *C30B 15/00* (2013.01); *C30B 35/002* (2013.01); *G01N 21/65* (2013.01)

(58) Field of Classification Search
CPC ... H01J 37/32935; G01N 21/64; G01N 21/65; G01N 21/68; G01N 21/95; G01N 21/3563; G01J 3/02; C30B 15/10; C30B 15/14; C30B 29/06
See application file for complete search history.

(56) References Cited

U.S. PATENT DOCUMENTS

| | | | |
|---|---|---|---|
| 2010/0127354 A1 | 5/2010 | Ono et al. | |
| 2010/0175611 A1* | 7/2010 | Takanashi | C30B 15/203 117/15 |

FOREIGN PATENT DOCUMENTS

| | | |
|---|---|---|
| JP | 2000103694 A | 4/2000 |
| JP | 2003151385 A | 5/2003 |
| JP | 2004292210 A | 10/2004 |
| JP | 2005320241 A | 11/2005 |
| JP | 2012116702 A | 6/2012 |

(Continued)

OTHER PUBLICATIONS

International Search Report (ISR) mailed Sep. 17, 2013, issued for International application No. PCT/JP2013/067946.
(Continued)

*Primary Examiner* — Abdullahi Nur
(74) *Attorney, Agent, or Firm* — Law Office of Katsuhiro Arai

(57) ABSTRACT

A quality-evaluated vitreous silica crucible for pulling silicon single crystal is provided, wherein an inner surface of the vitreous silica crucible has regions where surface defects including brown rings are to be generated when pulling silicon single crystal. The regions are distinguished using an infrared absorption spectrum or a Raman shift of the regions, wherein a position of each region and/or a density of the regions are/is specified.

4 Claims, 5 Drawing Sheets

(56) References Cited

FOREIGN PATENT DOCUMENTS

JP         2013112597 A     6/2013
JP         2013139353 A     7/2013

OTHER PUBLICATIONS

Notice of Allowance issued by U.S. Patent and Trademark Office, dated Jan. 17, 2017, for U.S. Appl. No. 15/377,963.

* cited by examiner

[Fig. 1]
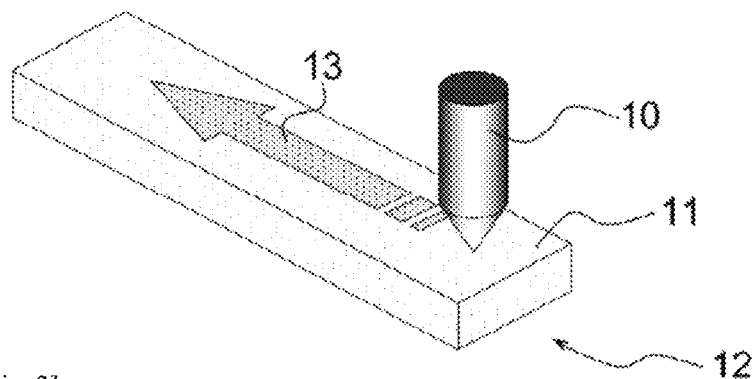
[Fig. 2]
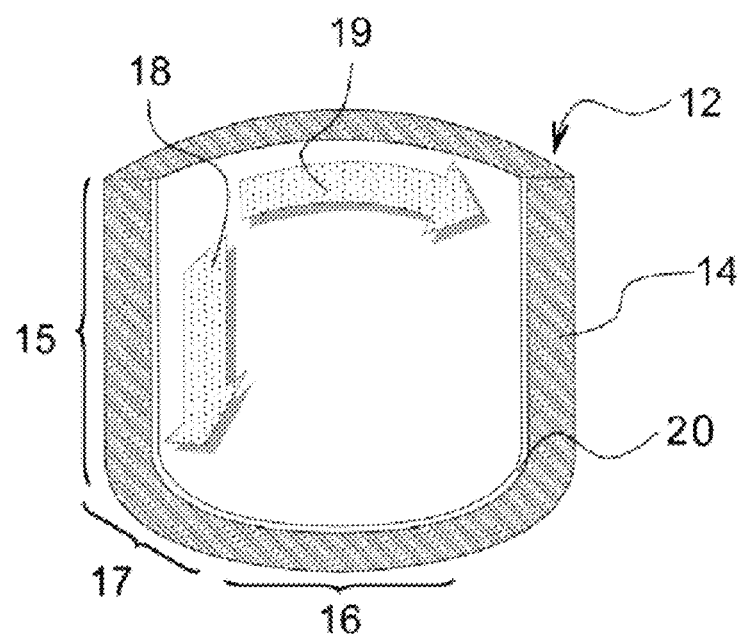

[Fig. 3]
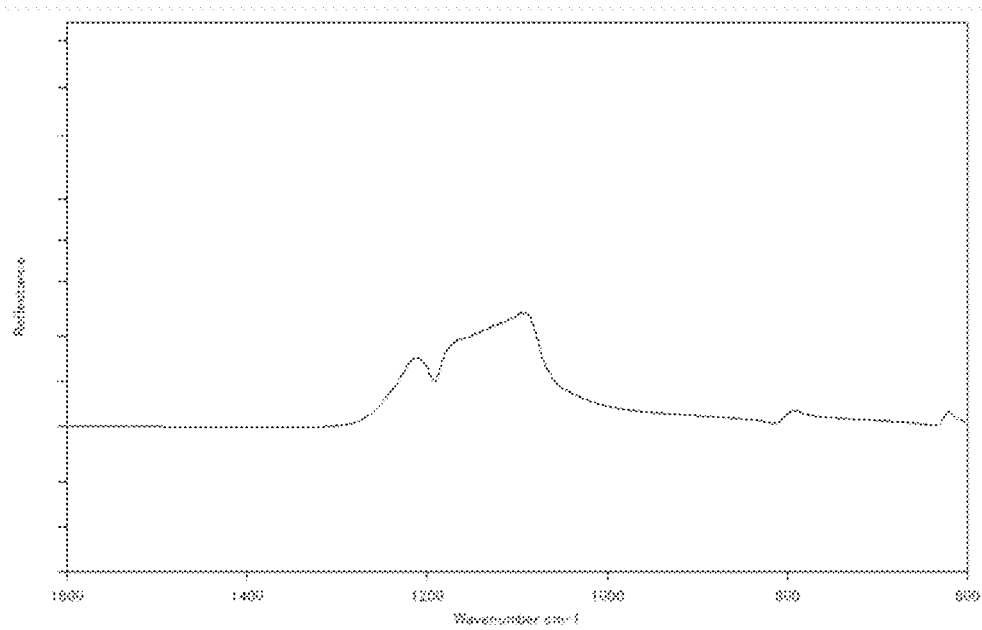
[Fig. 4]
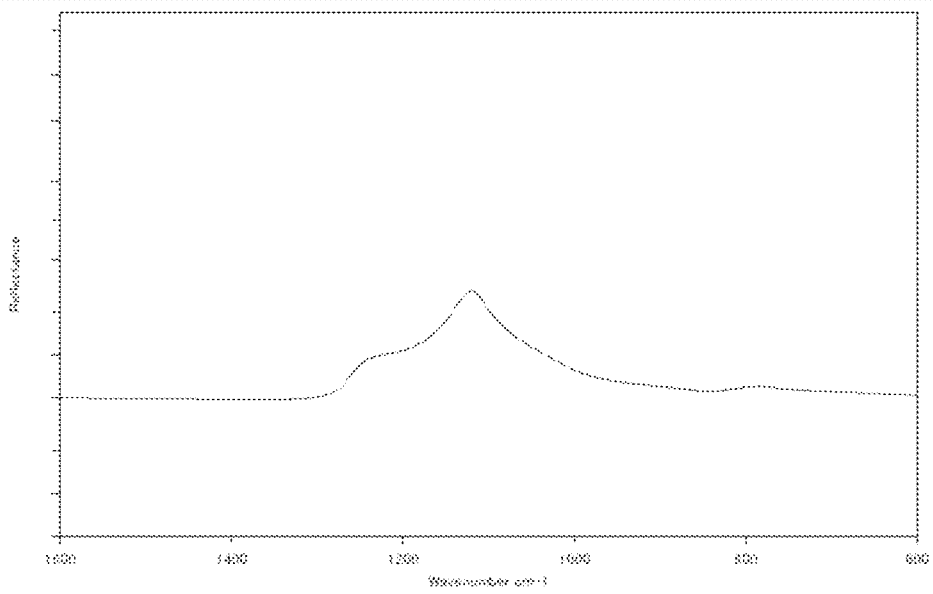

[Fig. 5]
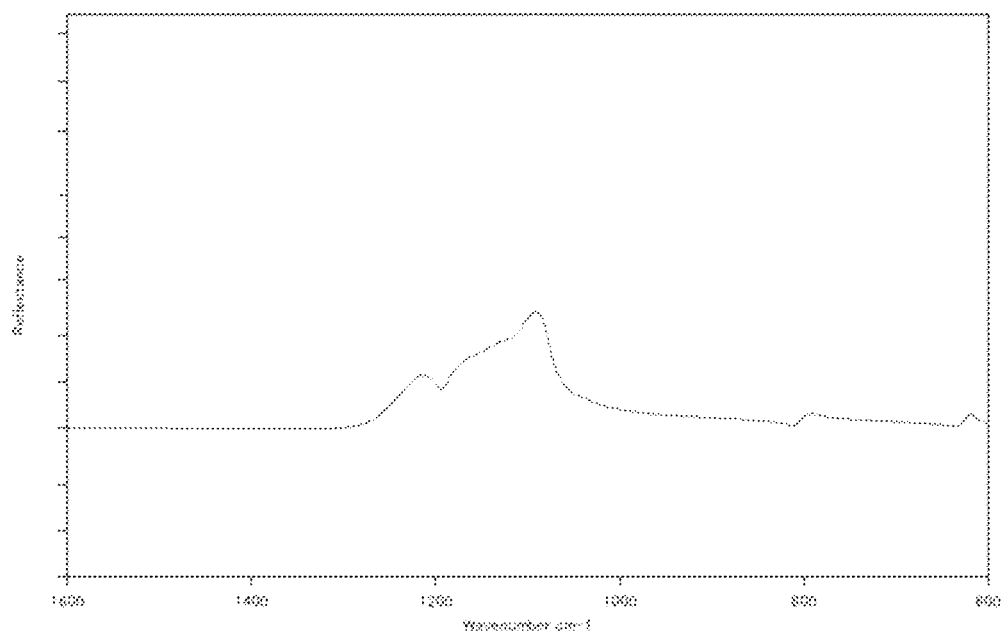
[Fig. 6]
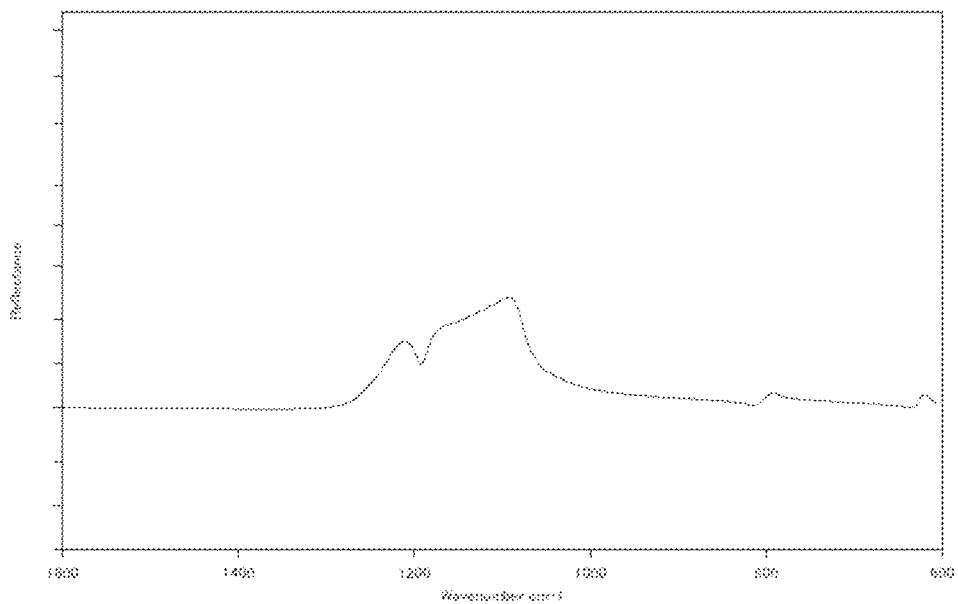

[Fig. 7]
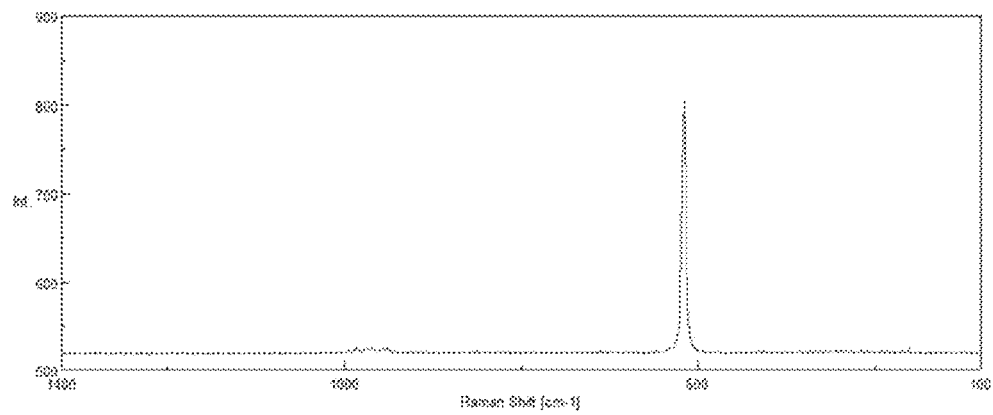
[Fig. 8]
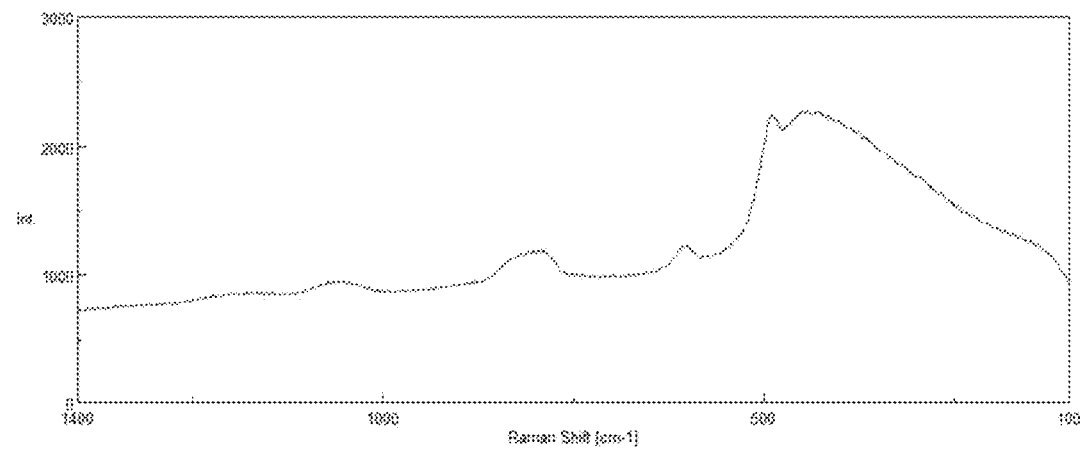
[Fig. 9]
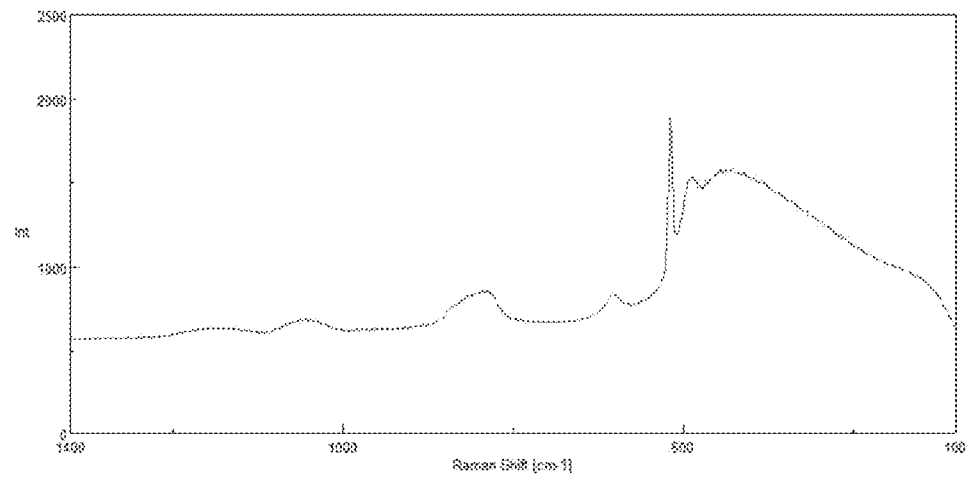

[Fig. 10]
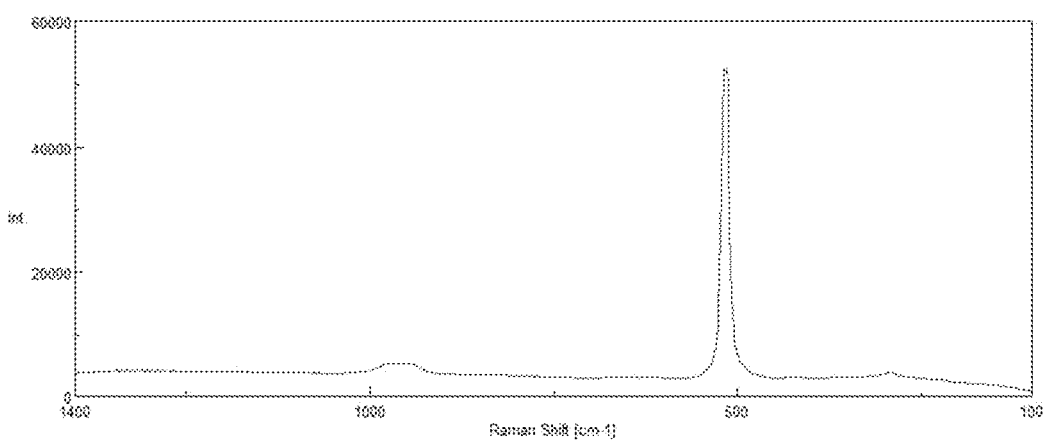

QUALITY-EVALUATED VITREOUS SILICA CRUCIBLE

TECHNICAL FIELD

The present invention relates to an inspection method of a vitreous silica crucible, for predicting a surface defect region of the vitreous silica crucible and determining a quality of the vitreous silica crucible.

BACKGROUND ART

In manufacture of a silicon single crystal, the Czochralski method (the CZ method) using a vitreous silica crucible has been employed. In this method, on a silicon melt surface at a high temperature of 1420° C. which is the melting point of silicon, a seed crystal is contacted to the melt surface while rotating in a horizontal direction, then pulled up gradually to manufacture a single crystal; and a vitreous silica crucible of high-purity is used in order to store the silicon melt.

In recent years, a diameter of the silicon single crystal has been increased owing to a demand for an efficiency of a semiconductor device process. As a result, a diameter of the vitreous silica crucible has also been increased. The size of the vitreous silica crucible is such as 28 inches (about 71 cm), 32 inches (about 81 cm), 36 inches (about 91 cm), and 40 inches (about 101 cm) in diameter. A crucible with a diameter of 101 cm is a huge crucible having a weight of about 120 kg, and the mass of silicon melt contained therein is 900 kg or more. That is, during the pulling of silicon single crystal, 900 kg or more silicon melt of about 1500 degrees C. is contained in the crucible. As a result, a distance from an external carbon heater to the center of the silicon single crystal, and an amount of melted polysilicon are increased, which causes the temperature in the vitreous silica crucible to become higher. Moreover, the pulling time may be prolonged, and a pulling may last 2 weeks or more. In order to maintain the solid-liquid interface of the silicon melt central part which is contacted with the single crystal near the silicon melting point of 1420 degrees C., the temperature of the vitreous silica crucible is as high as 1450-1600 degrees C. During maybe more than 2 weeks of pulling of silicon single crystal, the deformation amount for sidewall lowering of rim portion of the vitreous silica crucible may be 5 cm or more.

Brown cristobalite is generated on the inner surface of the vitreous silica crucible when contacting with the silicon melt at high temperature for a long time. As the pulling of a silicon single crystal is proceeded, cristobalite grows in horizontal direction and vertical direction with respect to the inner surface of the vitreous silica crucible to form a ring-shaped spot (brown ring). The formed brown ring is likely to be peeled off. The peeled-off brown ring is conveyed into the silicon single crystal when falling/mixing in the silicon melt. As a result, the pulled-up silicon ingot is polycrystallized, and the single crystallization yield is reduced.

Bubbles contained in the inner surface of the vitreous silica crucible are also a main cause of decrease in single crystallization yield. As erosion of the inner surface of the vitreous silica crucible is proceeded, the bubbles in the inner surface of the vitreous silica crucible enters the silicon melt. The single crystallization yield is reduced by the bubbles in the silicon melt being contained in the silicon ingot. In addition, under high temperature condition for a long time, bubbles contained in the inner surface of the vitreous silica crucible expand significantly. The expanded bubbles cause a deformation of the vitreous silica crucible and an ununiform inner surface. As a result, a melt surface vibration occurs in the silicon melt, and the single crystallization yield is reduced.

In order to solve such a problem, for example, Patent Document 1 proposed a method for pulling of silicon single crystal stably by limiting the number of brown rings in a predetermined position within a certain range (Japanese Patent Application Laid-Open No. 2005-320241). In addition, Patent Document 2 discloses that an amorphous component ratio of the vitreous silica crucible is identified by using laser Raman (Japanese Patent Application Laid-Open No. 2004-492210).

PRIOR ART DOCUMENTS

Patent Documents

Patent Documents 1: Japanese Patent Application Laid-Open No. 2005-320241
Patent Documents 2: Japanese Patent Application Laid-Open No. 2004-492210

SUMMARY OF THE INVENTION

Problems to be Solved by the Invention

However, in Patent Document 1, there still has problems such as it is difficult to limit the number of brown rings within certain range.

Moreover, in the method described in Patent Document 2, since the conditions for generating the surface defect regions of the brown rings or the like, are not disclosed until now, it is difficult to figure out in advance the crucible which is likely to generate surface defect regions before shipment.

In addition, the surface defect regions such as the brown rings may occur in the crucible inner surface during the pulling of silicon single crystal, but the ease of occurrence of surface defect regions differs for each crucible. That is, even the pulling of silicon single crystal is performed under a substantially same condition; the number of occurrence of surface defect regions is different for each crucible.

Accordingly, in consideration of such a situation, an object of the present invention is to provide an inspection method of vitreous silica crucible, for predicting the surface defect region of the vitreous silica crucible and determining the quality of the vitreous silica crucible.

Means for Solving the Problems

In order to solve at least one of the above-mentioned problems, the present inventors have made extensive research, and found out that by analyzing in detail a relationship between the infrared absorption spectrum and Raman shift, the generation of surface defect region of the vitreous silica crucible can be predicted. That is, the present invention is an inspection method of vitreous silica crucible, characterized by including: a measurement step of measuring an infrared absorption spectrum or a Raman shift of a measurement point on an inner surface of the vitreous silica crucible; a determining step of predicting whether a surface defect region is generated or not in the measurement point based on the obtained spectrum to determine the quality of the vitreous silica crucible.

BRIEF DESCRIPTION OF THE DRAWINGS

FIG. 1 is a schematic view showing a scanning state by a probe 10 on an inner surface 11 of a vitreous silica crucible made of a synthetic silica powder as raw material.

FIG. 2 is a cross section schematic view illustrating a scanning direction of the probe 10 in the crucible.

FIG. 3 is a reference infrared spectrum.

FIG. 4 is an infrared spectrum of a vitreous silica.

FIG. 5 is an infrared spectrum predicting a generation of surface defect region in the vitreous silica crucible before use.

FIG. 6 is an infrared spectrum of the vitreous silica crucible found surface defect region after use.

FIG. 7 is a reference Raman shift.

FIG. 8 is a Raman shift of a vitreous silica.

FIG. 9 is a Raman shift predicting a generation of surface defect region in the vitreous silica crucible before use.

FIG. 10 is a Raman shift of the vitreous silica crucible found surface defect region after use.

DESCRIPTION OF THE EMBODIMENTS

According to one aspect of the present invention, there is provided an inspection method, including: a measurement step of measuring an infrared absorption spectrum or a Raman shift of a measurement point on an inner surface of the vitreous silica crucible; a determining step of predicting whether a surface defect region is generated or not in the measurement point based on the obtained spectrum to determine the quality of the vitreous silica crucible. Hereinafter, the present invention will be explained in details.

[Vitreous Silica Crucible]

In the present invention, an inspection object of silica crucible, for example, as shown in the cross section view of FIG. 2, includes a substantially cylindrical straight body portion 15 having an opening on top end and extending in a vertical direction, a curved bottom portion 16, and a corner portion 17 connecting the straight body portion 15 with the bottom portion 16 and having a curvature larger than that of the bottom portion 16.

The vitreous silica crucible is preferred to include a transparent layer 20 on the inside and a bubble layer 14 on the outside thereof. The transparent layer 20 is a layer formed on the inside of the vitreous silica crucible, and is substantially bubble-free. The "substantially bubble-free" means a bubble content rate and bubble diameter at such a degree that a single crystallization yield does not decrease due to the bubbles. Here, the bubble content rate means the volume of the bubbles occupying in unit volume of the crucible. An image of the crucible inner surface is taken by use of an optical camera, and the crucible inner surface is divided based on a constant volume as a reference volume W1. A volume W2 occupied by bubbles is determined for the reference volume W1, and calculated by P (%)=(W2/W1) *100. The bubble layer 14, for example, has a content rate of bubbles contained therein of 0.2% or more and 1% or less, and the average diameter of the bubbles is 20 µm or more and 200 µm or less.

The vitreous silica crucible, for example, is manufactured as follows. The silica powder used for manufacturing a vitreous silica crucible includes crystallized natural silica powder and amorphous synthetic silica powder manufactured by chemical synthesis. The natural silica powder is silica powder manufactured by pulverizing natural mineral mainly composed of a-quartz. The synthetic silica powder can be manufactured by means of chemical synthesis such as gas phase oxidation of silicon tetrachloride ($SiCl_4$) (dry synthesis method), or hydrolysis of silicon alkoxide ($Si(OR_4)$) (sol-gel method).

First, a natural silica powder is applied to a mold used for vitreous silica crucible. Next, the vitreous silica crucible composed of an inner face layer (synthetic layer) vitrified from the synthetic silica powder and an outer face layer (natural layer) vitrified from the natural silica powder, is manufactured by supplying a synthetic silica powder on the natural silica powder, and melting the silica powder by Joule heat of arc discharge followed by cooling. In the initial stage of an arc melting step, bubbles are removed by subjecting the silica powder layer to a strong depressurization, thus a transparent vitreous silica layer (transparent layer) is formed, and subsequently, a vitreous silica layer (bubble layer) containing bubbles remained by weakening the depressurization is formed. Here, the inner face layer formed from the synthetic silica powder is not necessarily the same with the transparent layer. Moreover, the outer face layer formed from the natural silica powder is not necessarily the same with the bubble layer.

The melting of the silica powder is preferably performed so that the maximum temperature of the inner surface of the rotating mold is up to 2000-2600 degrees C. When the maximum temperature is lower than 2000 degrees C., the gas remained as bubbles during the manufacture of the vitreous silica or in the vitreous silica cannot be removed completely, and the crucible expands remarkably during the pulling of silicon single crystal. In addition, when the maximum temperature is higher than 2600 degrees C., the viscosity of the vitreous silica is reduced and the shape collapse may occur.

The arc melting is performed, for example, by arc discharge of alternate current three-phase (R phase, S phase, T phase). Therefore, in the case of alternate current three-phase, three carbon electrodes are used to generate arc discharge, thereby the silica powder layer is melted. The arc melting starts the arc discharge at the position where the tip of the carbon electrode is positioned higher than the opening portion of the mold. Thus, the silica powder layer near the opening portion of the mold is melt preferentially. Thereafter, the carbon electrode is lowered to melt the silica powder layer of the straight body portion, the corner portion and the bottom portion.

[Measurement Step]

In the present invention, an infrared absorption spectrum or a Raman shift of any measurement point on the inner surface of the vitreous silica crucible is measured. In order to enhance the accuracy of the quality determination of the vitreous silica crucible, it is preferred to have a plurality of measurement points. By measuring a plurality of positions, the number of generation of surface defect regions can be predicted in advance.

The infrared absorption spectrum can be measured using a Fourier transform infrared spectrophotometer (FT-IR). By irradiating infrared ray on the inner surface of the vitreous silica crucible, it is possible to investigate a change (molecular vibration) of the relative position between Si—O.

Specifically, for example, the infrared absorption spectrum can be measured as follows. The infrared absorption spectrum of the inner surface 11 of the vitreous silica crucible made of synthetic silica powder as raw material can be measured by using a probe 10 as shown in FIG. 1, which has a light source for irradiating the infrared ray and a light-receiving apparatus for receiving the reflected wave from the measurement object. The probe 10 can measure the infrared absorption spectrum of the inner surface 11 in a non-contact manner. As the measurement method, by providing the probe 10 to the inner surface 11 of the crucible 12 in a non-contact manner, and scanning toward the scanning direction 13, the infrared absorption spectrum can be measured. As other scanning mode, for example, a sample scanning mode and a light source scanning mode are exemplified. The sample scanning mode is a mode of driving a stage carrying the sample in XY direction to obtain an infrared absorption spectrum. The light source scanning mode is a mode of applying the light source in XY direction and moving the light-receiving apparatus matchingly to scan on the sample two-dimensionally. Any scanning mode may be employed.

The scanning direction, as shown in FIG. 2, may be a vertical direction 18 or horizontal direction 19 of the straight body portion 15. The scanning is not necessary to be performed on the entire crucible inner surface, and it is also possible to scan only a part of the inner surface 11 of the crucible. For example, it is possible to focus on scanning a position filled with polysilicon melt.

The probe 10 may be for example attached to a robot arm in order to avoid contacting with the inner surface 11. The robot arm may be placed on a rotating table having a rotary encoder which can detect the rotation angle. Thus, three-dimensional coordinate can be calculated easily. At this time, in order to avoid the contact between the probe 10 and the inner surface 11 and keep a constant spacing between the probe 10 and the inner surface 11, the robot arm may have a distance measurement unit. The distance measurement unit is preferred to have a semiconductor laser capable of measuring the distance to the inner surface of the vitreous silica crucible. The wavelength of the laser light is not especially limited, and a wavelength of 600-700 nm is preferable. Moreover, it is possible that, before the measurement of infrared absorption spectrum, the three-dimensional shape of the vitreous silica crucible is measured, and the robot arm is moved base on the measured three-dimensional shape to avoid the contact or to maintain the spacing between the probe 10 and the inner surface 11. The measurement spacing of the infrared absorption spectrum is, for example, 1-5 mm.

The Raman shift can be measured by Raman spectroscopy. In the Raman spectroscopy, light, such as a laser and the like, is irradiated to a sample to measure a scattered light caused by a movement of molecules having polarizability. In the vitreous silica, a peak related to a distortion structure due to the Si—O—Si bond angle, is detected.

The Raman shift can be measured by using the probe 10 or robot arm, as the measurement of the infrared absorption spectrum. The condition of the Raman measurement can be, for example, laser wavelength: 785 nm (100 mW), exposure time: 10 seconds, number of times of integration: 1 time. In the case of measuring the FT-IR measurement and the Raman measurement, either one can be measured previously, or both can be measured simultaneously.

[Determining Step]

In the determining step performed in the present invention, whether a surface defect region is generated in a measurement point or not, is predicted on the basis of the obtained spectrum. The "surface defect region" refers to an abnormal part or region generated in the vitreous silica crucible, which affects the yield of silicon single crystal. For example, it is a brown ring or bubble, or the like. Whether a surface defect region occurs or not, can be detected based on a spectrum peak. As the spectrum peak, for example, it may be all of or a part of the obtained spectrum peaks. In addition, it may be a characteristic peak within certain wavenumber range, and in this case, whether a surface defect region is generated or not can be predicted by only certain wavenumber range (band) of interest.

Specifically, for example, a generation of surface defect region can be predicted on the basis of following three methods and a combination thereof.

(1) Prediction Based on an Infrared Absorption Spectrum of Certain Wavenumber

The analysis result by the present inventors is to find that, the presence of peaks between wavenumber 1080-1100 $cm^{-1}$ and/or peaks between wavenumber 1150-1250 $cm^{-1}$, is the characteristic range of the generation of surface defect region. Therefore, it is possible to predict whether a surface defect region is generated or not by the presence of peaks in these ranges. Specifically, when there is a peak or there is no peak between wavenumber 1080-1100 $cm^{-1}$, it is possible to predict a generation of surface defect region. Also, when there is a peak between wavenumber 1150-1250 $cm^{-1}$, it is possible to predict a generation of surface defect region. In the case of determining quantitatively, it is also possible to carry out a determination by setting a threshold.

(2) Prediction Based on a Raman Spectrum of Certain Wavenumber

The analysis result by the present inventors is to find that, the presence of peaks between Raman shifts from 500 to 550 $cm^{-1}$, is the characteristic range of the generation of abnormal site. Therefore, it is possible to predict whether a surface defect region is generated or not by the presence of peaks in these ranges. In the case of determining quantitatively, it is also possible to carry out a determination by setting a threshold. Specifically, when a peak is present, it is possible to predict a generation of surface defect region.

(3) Prediction by a Comparison with Reference Spectrum

Whether a surface defect region is generated in a measurement point or not, is predicted by comparing the obtained spectrum with a reference spectrum prepared in advance. Here, the "reference spectrum prepared in advance" refers to, for example, a spectrum in the case of that in a measurement point of a vitreous silica crucible before pulling of silicon single crystal, a surface defect region is generated in the measurement point after the pulling of silicon single crystal. When the surface defect region is a brown ring, not only the region of the brown ring, but the center and a region near the center thereof are also included. The comparison using the reference spectrum prepared in advance may be compared immediately after measuring the spectrum of inner surface 11, or may be compared after measuring a plurality of measurement points. As a result of the comparison, the two spectra are determined to be equal or not, and in the case of unequal, a generation of surface defect region can be predicted. In the case of determining quantitatively, it is also possible to carry out a determination by setting a threshold. The comparison with the reference spectrum may utilize the predictions based on the (1) and (2) and compare only certain wavenumber range, to predict the generation of surface defect region.

By using previously accumulated data (the reference spectrum) under certain conditions, it is possible to carry out a comparison with higher accuracy in the practice under the same conditions. In addition, it is also possible to create a reference spectrum with high accuracy by feeding back the data.

From the prediction obtained as above, the quality of vitreous silica crucible is evaluated. For the evaluation of quality, for example, in the case of one position of measurement point, when a generation of surface defect region is predicted, it can be evaluated as a defective product. In the case of a plurality of measurement points, when a generation of a predetermined number of surface defect regions is predicted, it can be evaluated as a defective product.

In addition, in the case of a plurality of measurement points, the quality of the vitreous silica crucible can be determined based on a predicted generation number of the surface defect regions per unit area of inner surface of the vitreous silica crucible. The predicted generation number of the surface defect regions per unit area may be an average value. Further, it is possible to calculate the predicted generation number of the surface defect regions per unit area of certain portion (for instance, straight body portion, corner portion, and bottom portion) of the vitreous silica crucible, and the case of exceeding certain value is determined as a defective product. In this way, whether a vitreous silica crucible is defective or not can be easily determined even in a short measurement time.

[Method of Manufacturing Silicon Ingot]

A silicon ingot can be manufactured by (1) in a vitreous silica crucible 12, melting polysilicon to produce silicon melt, and (2) pulling up while rotating a seed crystal with the tip of the silicon seed crystal being soaked in the silicon melt. The shape of the silicon single crystal was made from: a cylindrical silicon seed crystal from the upper side, following a conical silicon single crystal, a cylindrical silicon single crystal having the same diameter as the bottom surface of the upper conical silicon single crystal, and a conical silicon single crystal having a vertex orienting downward.

The pulling of silicon ingot is usually performed at about 1450-1500 degrees C. After the pulling of silicon single crystal, the inner surface of the crucible is observed to confirm the presence of a brown ring. It is also possible to obtain the three-dimensional coordinates of the confirmed brown ring, and collate with the data during manufacturing the vitreous silica crucible 12 to make a data feedback.

EXAMPLES (Manufacture Example) Manufacture of Vitreous Silica Crucible

A vitreous silica crucible was manufactured on the basis of a rotating mold method. The mold opening diameter was 32 inch (81.3 cm), the average thickness of silica powder layer deposited on the mold inner surface was 15 mm, and the arc discharge was performed with three electrodes at 3-phase alternating current. The energization time of the arc melting step was 90 minutes, output was 2500 kVA, and the evacuation of the silica powder layer was started in 10 minutes from the start of energization. Three vitreous silica crucibles were manufactured. In the manufactured vitreous silica crucible, polysilicon was added to melt, and a silicon single crystal was pulled up.

(Reference Example 1) FT-IR Measurement and Raman Measurement

After the pulling of silicon single crystal, FT-IR measurement and Raman measurement of the brown ring generated on the inner surface of the crucible were performed.

FIGS. 3 to 6 are the results of measuring the microscopic infrared reflection spectrum using a microscopic infrared reflection measurement apparatus. The condition was: resolution: 4 cm$^{-1}$, number of times of integration: 64 times (about 30 seconds). FIG. 3 is a reference spectrum, and FIG. 4 is a spectrum of a vitreous silica. FIG. 6 is a spectrum of vitreous silica crucible found of surface defect region after use, and FIG. 5 is a spectrum predicting a generation of surface defect region in the vitreous silica crucible before use.

As shown in FIG. 6, for the surface defect region, peaks in vicinity of wavenumber 1210-1230 cm$^{-1}$ and wavenumber 1090-1094 cm$^{-1}$ were present. On the other hand, in the spectrum of the vitreous silica (not surface defect region), peak of the wavenumbers were not seen, and a peak in vicinity of wavenumber 1120 cm$^{-1}$ was present. This peak was not seen in FIG. 6. Therefore, it is understood that the peak between wavenumber 1080-1100 cm$^{-1}$ and peak between wavenumber 1150-1250 cm$^{-1}$ can be deemed as characteristic peaks, and also can be used as the reference spectrum.

FIGS. 7 to 10 are the results of measuring the Raman shift of the surface defect region using a dispersive type micro-Raman apparatus. The condition was: laser wavelength: 785 nm (100 mW), exposure time: 10 seconds, number of times of integration: 1 time. FIG. 7 is a reference spectrum, and FIG. 8 is a spectrum of vitreous silica. FIG. 10 is a spectrum of vitreous silica crucible found of surface defect region after use, and FIG. 9 is a spectrum predicting a generation of surface defect region in the vitreous silica crucible before use.

As shown in FIG. 9, for the surface defect region, a peak in vicinity of Raman shift 520-530 cm$^{-1}$ was present. On the other hand, in the vitreous silica (not surface defect region), the peak in Raman shift 520-530 cm$^{-1}$ was not present. Therefore, it is understood that the peak between Raman shifts from 500 to 550 cm$^{-1}$ can be deemed as characteristic peak, and also can be used as the reference spectrum.

Examples 1-3

The inner surfaces of three unused vitreous silica crucibles obtained in Manufacture Example were subjected to FT-IR measurement and Raman measurement. The three-dimensional shape of the inner face shape of the vitreous silica crucible was obtained, and the measurement on the straight body portion, the corner portion and the bottom portion of the vitreous silica crucible was carried out. The measurement point was selected arbitrarily from the region (a region of about 5 cm$^2$ square (about 25 cm$^2$) of above-mentioned portions of the vitreous silica crucible, and 20 points were measured respectively. The measurement range (spot diameter) of the FT-IR measurement and Raman measurement is 20 μm.

With respect to the FT-IR measurement, a spectrum with the characteristic peaks present in vicinity of wavenumber 1210-1230 cm$^{-1}$ and wavenumber 1090-1094 cm$^{-1}$ was observed. The measurement point observed of the characteristic peaks was deemed as the measurement point predicted of surface defect region generation, and the correspondent coordinates were stored in a storage device, thus the predicted generation index of the surface defect region was calculated. The generation index is a value obtained by dividing the total number of measurement positions by the observed number of the surface defect regions. The results are shown in Table 1.

With respect to the Raman measurement, a spectrum with the characteristic peak present in vicinity of Raman shift 520-530 cm$^{-1}$ was observed. The measurement point observed of the characteristic peaks was deemed as the measurement point predicted of surface defect region generation, and the correspondent coordinates were stored in a storage device, thus the predicted generation index of the surface defect region was calculated. The generation index is a value obtained by dividing the total number of measurement positions by the observed number of the surface defect regions. The results are shown in Table 1.

TABLE 1

| | crucible 1 | | | | | | crucible 2 | | | | | |
|---|---|---|---|---|---|---|---|---|---|---|---|---|
| | straight body portion | | corner portion | | bottom portion | | straight body portion | | corner portion | | bottom portion | |
| | IR | Raman | IR | Raman | IR | Raman | IR | Raman | IR | Raman | IR | Raman |
| Predicted generation index | 0.10 | 0.15 | 0.15 | 0.15 | 0.10 | 0.20 | 0.05 | 0.05 | 0.05 | 0.10 | 0.10 | 0.15 |

| | crucible 3 | | | | | |
|---|---|---|---|---|---|---|
| | straight body portion | | corner portion | | bottom portion | |
| | IR | Raman | IR | Raman | IR | Raman |
| Predicted generation index | 0.10 | 0.15 | 0.10 | 0.10 | 0.05 | 0.10 |

After the FT-IR measurement and Raman measurement, a pulling of silicon single crystal using the measured vitreous silica crucible was carried out. On the basis of the coordinates corresponding to the characteristic peaks of the FT-IR measurement and Raman measurement before the pulling of single crystal, the inner surface of the vitreous silica crucible after the pulling of single crystal was confirmed. As a result, in the coordinates in which the characteristic peaks were present, surface defect regions on the inner surface of the vitreous silica crucible after the pulling of single crystal were observed. Table 2 is a list of the generation number of surface defect regions per about 25 cm$^2$ of the measurement region.

TABLE 2

| | Crucible 1 | | | Crucible 2 | | | Crucible 3 | | |
|---|---|---|---|---|---|---|---|---|---|
| | straight body portion | corner portion | bottom portion | straight body portion | corner portion | bottom portion | straight body portion | corner portion | bottom portion |
| generation number | 25 | 23 | 33 | 10 | 9 | 20 | 22 | 15 | 18 |

From the above results, it is understood that, in the case of FT-IR measurement, the peak in vicinity of wavenumber 1210-1230 cm$^{-1}$ and/or peak in vicinity of wavenumber 1090-1094 cm$^{-1}$ can be used as a determination criterion to determine whether a crucible is likely to generate a surface defect region or not. In the case of Raman measurement, the peak of Raman shift 520-530 cm$^{-1}$ can be used as a determination criterion to determine whether a crucible is likely to generate a surface defect region or not. Further, by combining the criterion of FT-IR measurement and the Raman measurement, it is possible to inspect the generation site of the surface defect region more precisely.

According to the inspection method of the present invention, it is possible to specify the generation position of the surface defect region before the pulling of silicon single crystal. Therefore, the generation ratio or density of the surface defect regions can be predicted in advance, and the quality inspection of the surface defect region for the vitreous silica crucible before shipment can be performed, which was not possible so far. Further, the quality inspection of a vitreous silica crucible required certain density of surface defect regions, can be performed.

This application is a continuation of U.S. patent application Ser. No. 15/377,963, filed Dec. 13, 2016 which is a continuation of U.S. patent application Ser. No. 14/901,030, filed Dec. 27, 2015, now U.S. Pat. No. 9,557,276, which is the U.S. National Phase under 35 U.S.C. §371 of International Application PCT/JP2013/067946, filed Jun. 30, 2013, each disclosure of which is herein incorporated by reference in its entirety. The International Application was published under PCT Article 21(2) in a language other than English. The applicant(s) herein explicitly rescind(s) and retract(s) any prior disclaimers or disavowals made in any parent, child or related prosecution history with regard to any subject matter supported by the present application.

What is claimed is:

1. A quality-evaluated vitreous silica crucible for pulling silicon single crystal, wherein an inner surface of the vitreous silica crucible has regions where surface defects including brown rings are to be generated when pulling silicon single crystal, said regions being distinguished using an infrared absorption spectrum or a Raman shift of the regions, wherein a position of each region and/or a density of the regions are/is specified.

2. The quality-evaluated vitreous silica crucible according to claim 1, wherein the position of each region corresponds to a position having a peak in the infrared absorption spectrum corresponding to wavenumber 1080-1100 cm$^{-1}$ and/or wavenumber 1150-1250 cm$^{-1}$.

3. The quality-evaluated vitreous silica crucible according to claim 1, wherein the position of each region corresponds to a position having a peak in the Raman shift corresponding to Raman shift 500-550 cm$^{-1}$.

4. The quality-evaluated vitreous silica crucible according to claim 1, which has a substantially cylindrical straight body portion having an opening on a top end and extending in a vertical direction, a curved bottom portion, and a corner portion connecting the straight body portion with the bottom portion and having a curvature larger than that of the bottom portion, wherein the density of the regions is specified in each of the body portion, the curved bottom portion, and the corner portion.

\* \* \* \* \*